United States Patent [19]

Hosoi et al.

[11] Patent Number: 4,834,071
[45] Date of Patent: May 30, 1989

[54] ILLUMINANCE CONTROLLER FOR LIGHT SOURCE AND ENDOSCOPE INCLUDING THE SAME

[75] Inventors: Sugao Hosoi; Hiromichi Akutsu, both of Tochigi, Japan

[73] Assignee: Kabushiki Kaisha Toshiba, Kawasaki, Japan

[21] Appl. No.: 218,149

[22] Filed: Jul. 13, 1988

[30] Foreign Application Priority Data

Jul. 13, 1987 [JP] Japan .................................. 62-172829
Nov. 27, 1987 [JP] Japan .................................. 62-297346

[51] Int. Cl.$^4$ .............................................. A61B 1/06
[52] U.S. Cl. ......................................... 128/6; 362/282; 358/98
[58] Field of Search ..................... 128/4, 6; 358/98; 362/277, 282

[56] References Cited

U.S. PATENT DOCUMENTS

| | | | |
|---|---|---|---|
| 4,407,272 | 10/1983 | Yamaguchi | 128/6 |
| 4,425,599 | 1/1984 | Rieder et al. | 362/277 X |
| 4,444,462 | 4/1984 | Ono et al. | 128/6 X |
| 4,625,236 | 11/1986 | Fujimori et al. | 358/98 |
| 4,710,807 | 12/1987 | Chikama | 358/98 |
| 4,729,018 | 3/1988 | Watanabe et al. | 362/282 X |

*Primary Examiner*—William H. Grieb
*Attorney, Agent, or Firm*—Foley & Lardner, Schwartz, Jeffery, Schwaab, Mack, Blumenthal & Evans

[57] ABSTRACT

An illuminance controller of a light source for use in an endoscope or the like, including a diaphragm for cutting a light beam generated by the light source to control an illuminance of the light beam, in which the light beam cut amount of the diaphragm is controlled by a diaphragm controller, and in which the illuminance of the light beam cut by the diaphragm varies with respect to a driving amount of a drive motor in accordance with an exponential function.

13 Claims, 12 Drawing Sheets

ILLUMINANCE CONTROLLER FOR LIGHT SOURCE AND ENDOSCOPE INCLUDING THE SAME

BACKGROUND OF THE INVENTION

1. Field of the Invention

The present invention relates to an illuminance controller of a light source and an endoscope including the same, which is capable of controlling an illuminance of a light beam in an accurate and ready manner without causing any problem such as an overshoot, a hunting or a responsive lag, and producing an uniform illuminance distribution of a light beam over an entire illuminated area.

2. Description of the Prior Art

An endoscope has been widely used for a medical treatment or inspection of organs such as the duodenum, the rectum, the colon, the esophagus, the stomach and so forth.

A conventional electronic endoscope comprises a scope for observing the inside of an internal organ, a light source for generating a light beam, and an operational unit for operating picture signals picked up by the scope. The scope includes an end portion having an optoelectronic photographing element such as a charge coupled device (CCD), and an optical system for observing an object, a flexible intermediate portion having a light guide composed of optical fibers and electric wires therein, a manual operating handle portion. The light source includes a light source lamp for generating the light beam and a condenser lens for collecting the light beam emitted by the lamp to feed the light beam to the light guide.

In this case, when a luminous energy or an illuminance of a light beam to be fed to the light guide is too much, a halation or blooming arises in an observing area of the object to be observed by the CCD, and, when the illuminance of the light beam is too small, it is difficult to ensure a sufficient observing visual filed. Therefore, during an operation using the endoscope, the illuminance of the light beam to be fed to the light guide is controlled to a proper intensity.

In FIGS. 1 and 2, there is shown a conventional illuminance controller for use in a light source of an endoscope, and the illuminance controller comprises a pair of shutter plates 1 and 2 movably mounted between a condenser lens 3 and a rear end 5 of a light guide 4. The shutter plates 1 and 2 are slidably moved in opposite directions indicated by an arrow a in FIG. 1, perpendicular to a light path of a light beam 6 generated by a lamp (not shown), for partially or entirely opening or closing the light path of the light beam 6 to control the illuminance of the light beam 6 to be fed to the rear end 5 of the light guide 4. The shutter plates 1 and 2 functions as a diaphragm or a lens stop.

In FIGS. 3 and 4, there is shown another conventional illuminance controller, like the controller shown FIG. 1, having a similar construction thereto, except that a fishtail-like shutter plate 7 is movably mounted between the condenser lens 3 and the rear end 5 of the light guide 4. The fishtail-like shutter plate 7 is moved in a direction indicated by an arrow b in FIG. 3 so as to open or close the light path of the light beam 6 for controlling the illuminance of the light beam 6 in the same manner as the previous embodiment of FIG. 1. The fishtail-like shutter plate 7 acts as a diaphragm or a lens stop as well.

However, in the conventional illuminance controllers described above, the diaphragm is adapted to adjust the illuminance of the light beam corresponding to a rotation of a drive motor. Accordingly, the variation rate of the illuminance of the light beam largely depends on a rotative angle $\theta$ of the drive motor, as indicated by a curve A in FIG. 6. That is, the variation rate of the illuminance of the light beam is represented by $\Delta I/I$ wherein I is the illuminance of the light beam and $\Delta I$ is the variation of the illuminance corresponding to the rotation of the drive motor. As to the curve A in FIG. 6, when the rotative angle $\theta_1$ is small, the variation rate $\Delta I_1/I_1$ of the illuminance becomes large, and, in turn, when the rotative angle $\theta_2$ is large, the variation rate $\Delta I_2/I_2$ of the illuminance becomes small.

Accordingly, when the rotative angle $\theta$ of the drive motor is small, it is liable to produce an overshoot or a hunting, and, when the rotative angle $\theta$ is large, a responsive lag arises. In both cases, It is quite difficult to suitably adjust the illuminance of the light beam to a desired value.

Further, in the conventional illuminance controllers shown in FIGS. 1 to 4, the illuminance of the light beam to be fed to the light guide 4 is controlled by cutting the light path of the light beam 6 using the shutter plates 1 and 2 or the fishtail-like shutter plate 7 slidably arranged between the condenser lens 3 and the light guide 4, and the light guide 4 emits the light beam 6 only to the same angular direction as the incident angle of the light beam 6. Hence, the control of the illumination of the light beam can be readily carried out, but the distribution characteristics of the light beam such as the light intensity distribution or the illuminance distribution of the light beam emitted from the light guide 4 to the object to be observed becomes uneven over the illuminated area with the variation depending on the cut amount of the light beam. As a result, the desired uniform illuminance may not be obtained in all area of the observed visual field. When the object is observed by using this endoscope, the light intensity remarkably changes in a picture depending on the distance and the area of the object, and it often becomes difficult to observe the object.

In order to remove such a problem, a snail-like rotary shutter plate 8 having a spiral periphery for cutting the light path of the light beam has been proposed, as shown in FIG. 5. In this embodiment, the illuminance of the light beam for illuminating the object is varied in order to maintain the brightness of the picture of the object to a certain value by changing the axial distance between the optical axis of the light beam and the rotary axis of the rotary shutter plate 8 depending on the brightness of the picture, thereby controlling the irradiation time of the pulsed light beam.

In this case, when the luminous intensity of the light beam generated by the light source is constant, the illuminance of the light beam is in proportion to its irradiation time. When the rotational speed of the rotary shutter plate 8 is constant, assuming that the axial distance between the rotary axis of the rotary shutter plate 8 and the optical axis of the light beam is r, the irradiation time is proportional to an opening angle $\theta$ which is defined by an initial side 8a of the angle $\theta$ and an angle generating line 8b passing through the center of the rotary shutter plate 6 and an intersection of the spiral periphery of the rotary shutter plate 8 and the circumference of a circle having a radius r around the center of the rotary shutter plate 8.

In the rotary shutter plate 8 shown in FIG. 5, $r_0$ is the minimum value of the radius r, and $r-r_0$ is an effective axial distance. The opening angle $\theta$ of the rotary shutter plate 8 is formed to satisfy a formula $\theta = k(r-r_0)$, wherein k is constant, as shown by a straight line G in FIG. 18, in which the irradiation time of the light beam is represented by the opening angle $\theta$. Therefore, the opening angle $\theta$ always varies with the constant variation rate, and thus the illuminance, i.e., the irradiation time of the light beam varies in proportion to the axial distance r.

However, in this embodiment, since the opening angle $\theta$ corresponding to the illuminance or the irradiation time of the light beam is proportional to the axial distance r, when the axial distance r is varied, the variation rate $\Delta\theta/\theta$ of the opening angle $\theta$ is changed largely depending on the axial distance r.

Accordingly, even if the illuminance of the light beam is varied with a certain rate depending on the object to be photographed, the variation amount $\Delta r$ of the axial distance r varies in various ways. When the variation amount $\Delta r$ of the axial distance r is small, for instance, in case of a pulse motor for driving the rotary shutter plate, a speed reducer having a sufficiently large speed reduction ratio is required. However, in this case, when the variation amount $\Delta r$ becomes large, i.e., it is required to rotate the output shaft of the speed reducer at a high speed, it becomes inconvenient.

Further, when the irradiation time of the light beam is automatically controlled in order to maintain the illuminance of the light beam for illuminating the object to the fixed value, if a feedback gain is determined so as to obtain a stable motion when the angle variation rate $\Delta\theta/\theta$ is large, it becomes liable to occur a responsive lag when the angle variation rate $\Delta\theta/\theta$ is small. Thus, in an automatic illuminance control system, it becomes impossible to prevent as a whole the problems such as the overshoot, the hunting, the responsive lag and the like.

SUMMARY OF THE INVENTION

Accordingly, it is an object of the present invention to provide an illuminance controller of a light source and an endoscope including the same, free from the aforementioned disadvantages and defects of the prior art, which is capable of preventing an overshoot, a hunting and a responsive lag, controlling an illuminance of a light beam in an accurate and ready manner, producing a uniform illuminance distribution of a light beam over an entire illuminated area, and readily obtaining a quick response in an automatic illuminance control system.

In accordance with one aspect of the present invention, there is provided an illuminance controller for a light source, and an endoscope comprising a diaphragm for cutting a light beam generated by a light source to control an illuminance of the light beam, diaphragm control means for controlling a light beam cut amount of the diaphragm, and drive means for driving the diaphragm, the illuminance of the light beam cut by the diaphragm varying with respect to a driving amount of the drive means in accordance with an exponential function.

In accordance with another aspect of the present invention, there is provided an illuminance controller for a light source, and an endoscope comprising a diaphragm for cutting a light beam generated by a light source to control an illuminance of the light beam, diaphragm control means for controlling a light beam cut amount of the diaphragm, and drive means for driving the diaphragm control means, the illuminance I of the light beam cut by the diaphragm varying with respect to a rotative angle $\theta$ of the drive means in accordance with a formula $I\alpha \exp^{K\theta}$, wherein K is constant.

In accordance with a further aspect of the present invention, there is provided an illuminance controller for a light source, and an endoscope comprising a diaphragm for cutting a light beam generated by a light source to control an illuminance of the light beam, drive means for driving the diaphragm, and diaphragm control means for controlling a light beam cut amount of the diaphragm, the illuminance of the light beam cut by the diaphragm varying with respect to an axial distance R between an optical axis of the light beam and a rotary axis of the diaphragm in accordance with a formula $I\alpha \exp^{kR}$, wherein k is constant.

BRIEF DESCRIPTION OF THE DRAWINGS

Above and other objects, features and advantages of the present invention will more fully appear from the following description of the preferred embodiments with reference to the accompanying drawings, in which.

DESCRIPTION OF THE PREFERRED EMBODIMENTS

Figure 3:
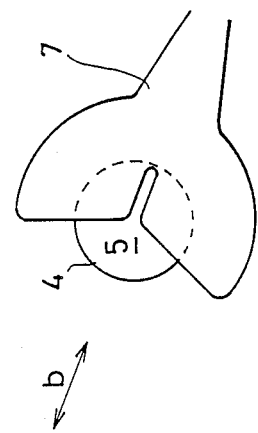
FIG. 3 is a front view of another conventional illuminance controller of the light source for use in the endoscope.
Figure 4:
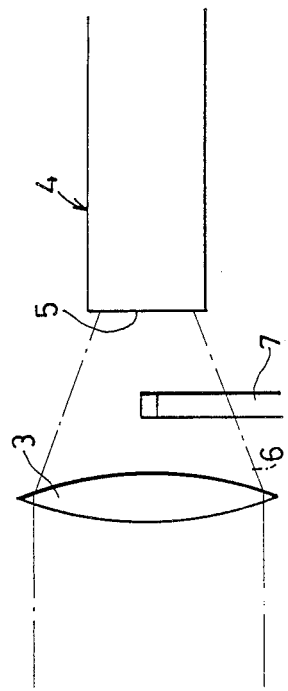
FIG. 4 is a top view of FIG. 3.
Figure 1:
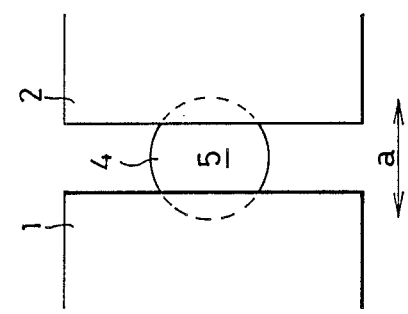
FIG. 1 is a front view of a conventional illuminance controller of a light source for use in an endoscope.
Figure 2:
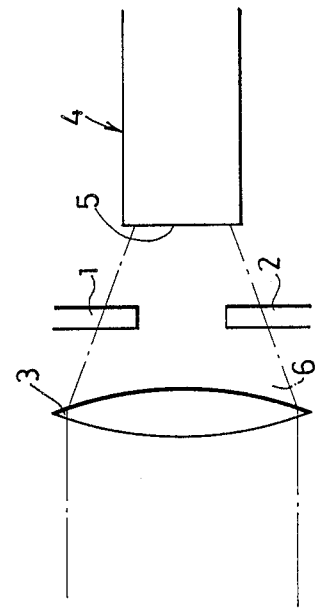
FIG. 2 is a top view of FIG. 1.
Figure 6:
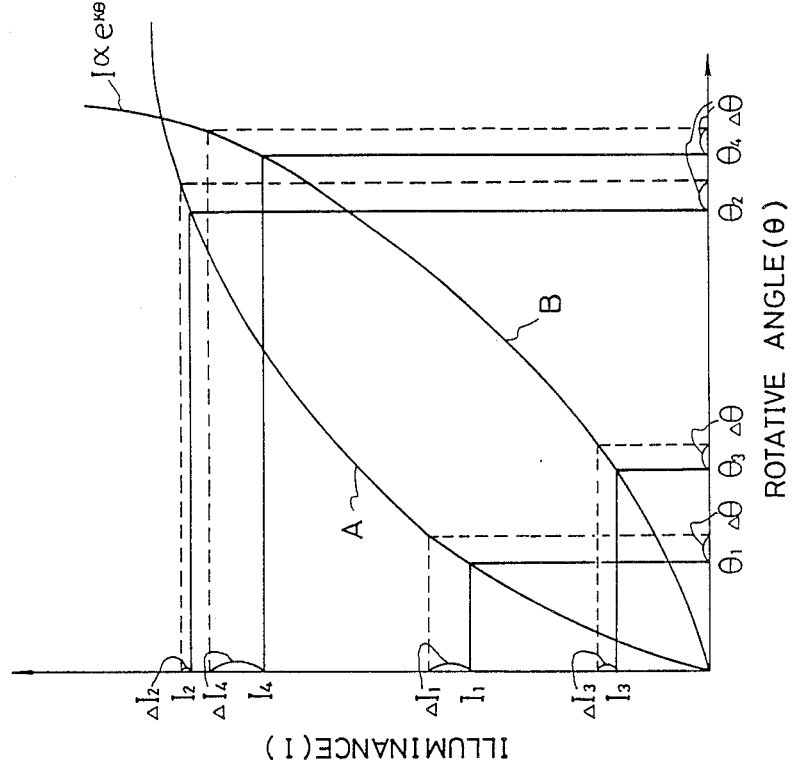
FIG. 6 is a graphical representation showing a relation between a rotative angle and an illuminance of a diaphragm of an illuminance controller of a light source for use in an endoscope according to the present invention as compared with a conventional diaphragm.
Figure 7:
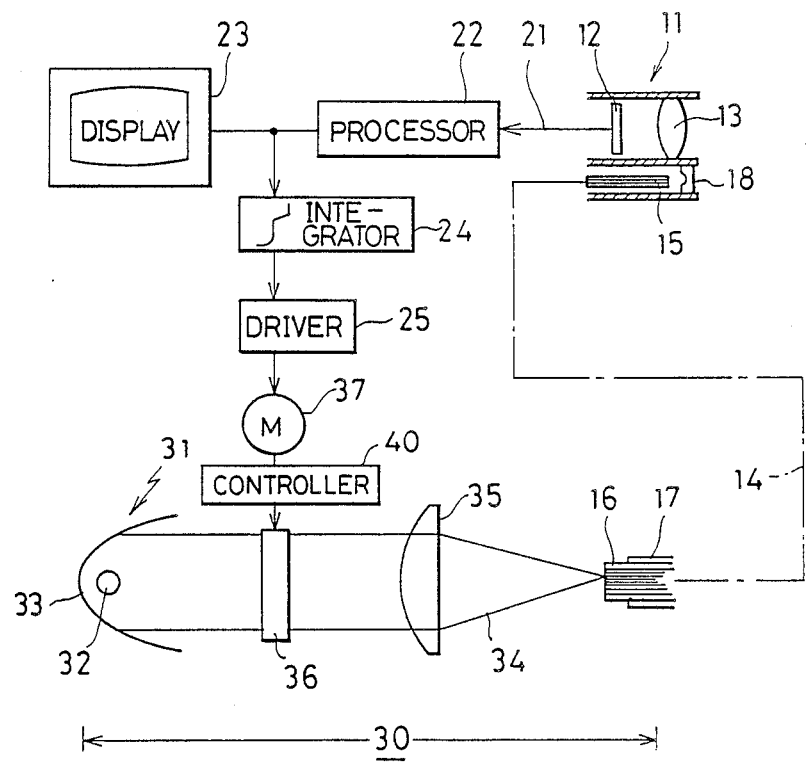
FIG. 7 is a schematic block diagram of an endoscope including one embodiment of an illuminance controller for a light source according to the present invention.

Referring now to the drawings, wherein like reference characters designate like or corresponding parts throughout the several views, there is shown in FIGS. 7 an endoscope including one embodiment of an illuminance controller for a light source according to the present invention. FIG. 6 shows a relation between a rotative angle $\theta$ and an illuminance I of a diaphragm of the illuminance controller of FIG. 7 in comparison with a conventional illuminance controller.

In FIG. 7, the endoscope includes a scope having an end portion 11, and a charge coupled device (CCD) 12 for photographing an object, an object lens 13, a front end 15 of a light guide 14 and a lighting window 18 are provided in the end portion 11 of the scope. The CCD 12 outputs picture signals to a signal processor 22 via a cable 21, and the processor 22 sends processed signals to a display 23 for monitoring pictures therein and to an integrator 24. The integrator 24 outputs a signal to a driver 25 for driving a reversible motor 37.

A light source 30 includes a light source portion 31 having a lamp 32 for generating a light beam 34 and a reflecting mirror 33, a condenser lens 35 and a diaphragm 36 arranged in the light path of the light beam 34 between the light source portion 31 and the condenser lens 35, for partially or entirely cutting the light beam 34 to control the illuminance of the light beam 34. The light beam 34 generated by the lamp 32 is reflected by the mirror 33 to produce the approximately parallel light beam 34, and then the parallel light beam 34 passes through the diaphragm 36 and is then converged to a rear end 16 of the light guide 14 by the condenser lens 35. The rear end 16 of the light guide 14 is supported by a light guide jack 17. The drive motor 37 for driving the diaphragm 36 is connected to the diaphragm 36 via a diaphragm controller 40 for controlling the light beam cut amount of the diaphragm 36.

The diaphragm controller 40 pivots the diaphragm 36 by means of the drive motor 37 to control the light beam cut amount of the diaphragm 36 so that the illuminance I of the light beam 34 cut by the diaphragm 36 may be varied along a curve B in FIG. 6, the curve B representing $I\alpha exp^{K\theta}$, wherein K is constant, with respect to the rotative angle $\theta$ of the drive motor 37. In this embodiment, when the drive motor 37 is rotated $\Delta\theta$, the illuminance I of the light beam 34 is changed by $\Delta I \alpha K\Delta\theta . exp^{K\theta}$, and a relative variation $\Delta I/I$ of the illuminance becomes $K\Delta\theta$. Therefore, when the rotating speed $\omega$ of the drive motor 37 is constant, a variation rate of the illuminance I of the light beam 34 becomes a constant value of $\Delta I/I = K\omega$.

Figure 8:
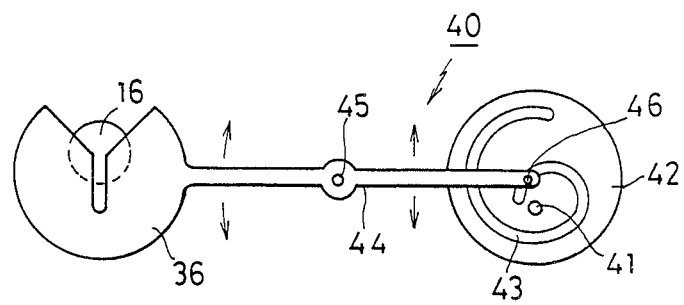
FIG. 8 is a front view of one embodiment of a diaphragm controller shown in FIG. 7.

In FIG. 8, there is shown one embodiment of the diaphragm controller 40 comprising a cam member 42 having a spiral guide groove 43 thereon, connected to a rotary shaft 41 of the drive motor 37, a pivot arm member 44 pivotally mounted to a pivot pin 45, and a guide pin member 46 secured to one end of the pivot arm member 44. The other end of the pivot arm member 44 is integrally connected to one side of the diaphragm 36 comprised of a fishtail-like shutter plate, and the guide pin member 46 connected to the pivot arm member 44 engages with the spiral guide groove 43 of the cam member 42. In this embodiment, the spiral guide groove 43 of the cam member 42 is so formed that the relation between the rotative angle $\theta$ of the rotary shaft 41 of the drive motor 37 and the illumination I of the light beam 34 passing through the diaphragm 36 may be represented by the curve B ($I\alpha exp^{K\theta}$) in FIG. 6.

When an order for controlling the illuminance of the light beam is given to the driver 25, the driver 25 drives the drive motor 37, and in synchronism with the rotation of the rotary shaft 41 of the drive motor 37 at the constant speed, the cam member 42 is rotated. Then, the guide pin member 46 is pivoted along the spiral guide groove 43 of the cam member 42 and thus the diaphragm 36 is also pivoted via the pivot arm member 44 and the pivot pin 45. The diaphragm 36 cuts the light path of the light beam 34, and the light beam 34 having the illuminance $I\alpha exp^{K\theta}$ with respect to the rotative angle $\theta$ of the drive motor 37 is fed to the rear end 16 of the light guide 14.

Figure 9:
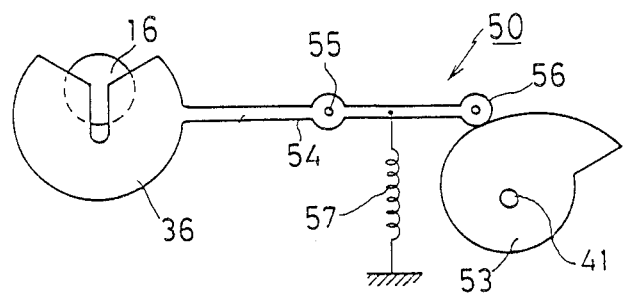
FIG. 9 is a front view of another embodiment of the diaphragm controller of FIG. 7.

In FIG. 9, there is shown another embodiment of the diaphragm controller 50 having a similar construction to the embodiment shown in FIG. 8. In this case, a cam member 53 has a spiral periphery whose shape is similar to the spiral guide groove 43 of the cam member 42 of the previous embodiment, and a slider member 56 is attached to one end of the pivot arm member 54 and is biased to make contact with the spiral periphery of the cam member 53 by a spring member 57. The pivot arm member 54 is pivotally mounted to a pivot pin 55, and the other end of the pivot arm member 54 is integrally connected to one side of the diaphragm 36.

In this embodiment, when the cam member 53 is rotated by the rotary shaft 41 of the drive motor 37 in the same manner as the previous embodiment, the pivot arm member 54 is pivoted through the slider member 56 contacting the spiral periphery of the cam member 53, and thus the diaphragm 36 is pivoted in the same manner as the previous embodiment, with the result of the same effects and advantages as those of the previous embodiment.

From the above description of the first embodiment of the illuminance controller and an endoscope of the present invention, it is readily understood that the diaphragm is controlled by the diaphragm controller so that the diaphragm may change the illuminance I of the light beam to the value $I\alpha exp^{K\theta}$ represented by the curve B in FIG. 6 with respect to the rotative angle $\theta$ of the drive motor. Hence, when the drive motor is rotated at the constant speed, the variation rate $\Delta I/I$ of the illuminance of the light beam to be fed to the light guide becomes constant at any rotative angle of the drive motor. Therefore, according to the present invention, an excellent automatic illuminance control of the light beam can be performed throughout the entire rotative angles of the drive motor without causing any problem such as an overshoot, a hunting or a delayed response.

Thus, the illuminance control of the light beam for lighting the object can be accurately and readily carried out, and, when the present invention is applied to an endoscope, the efficiency of the medical inspection and treatment can be remarkably improved.

Figure 10:
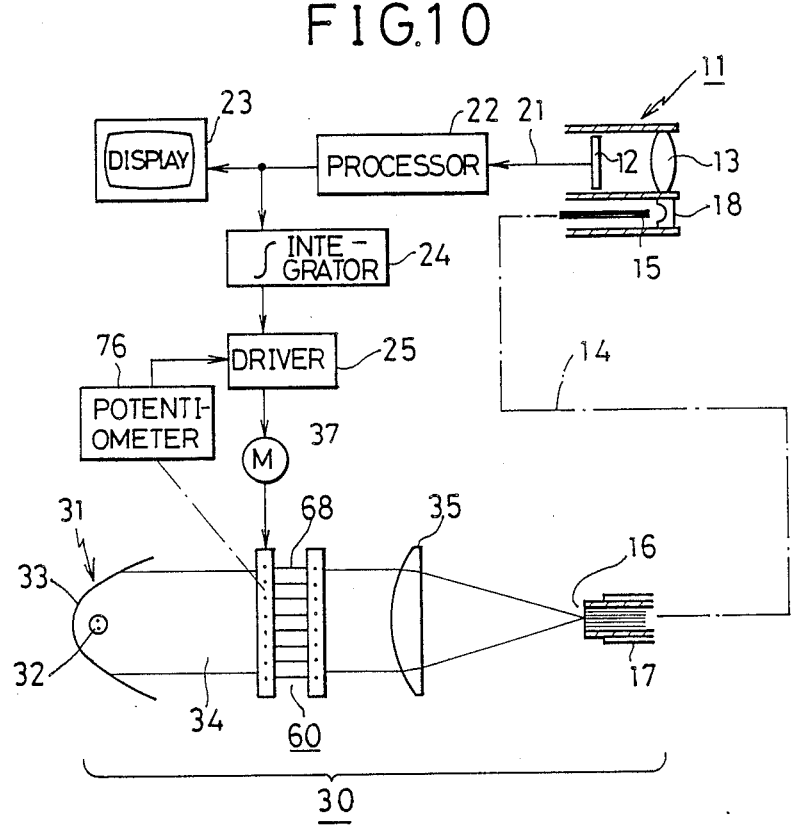
FIG. 10 is a schematic block diagram of another endoscope including another embodiment of an illuminance controller for a light source according to the present invention.

In FIG. 10, there is shown another endoscope including the second embodiment of the illuminance controller for the light source according to the present invention.

In this case, the endoscope has a similar structure to the first embodiment shown in FIG. 7, except that an illuminance control device 60 includes a diaphragm having a plurality of shutter plates 68, a diaphragm controller for controlling the diaphragm, and a potentiometer 58.

Figure 11:
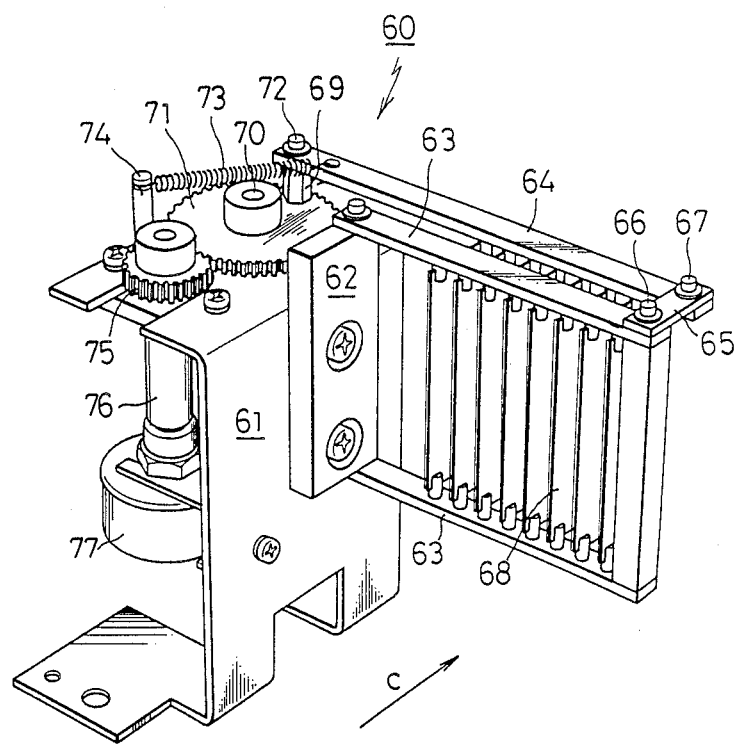
FIG. 11 is a perspective view of one embodiment of an illuminance control device shown in FIG. 10.
Figure 12:
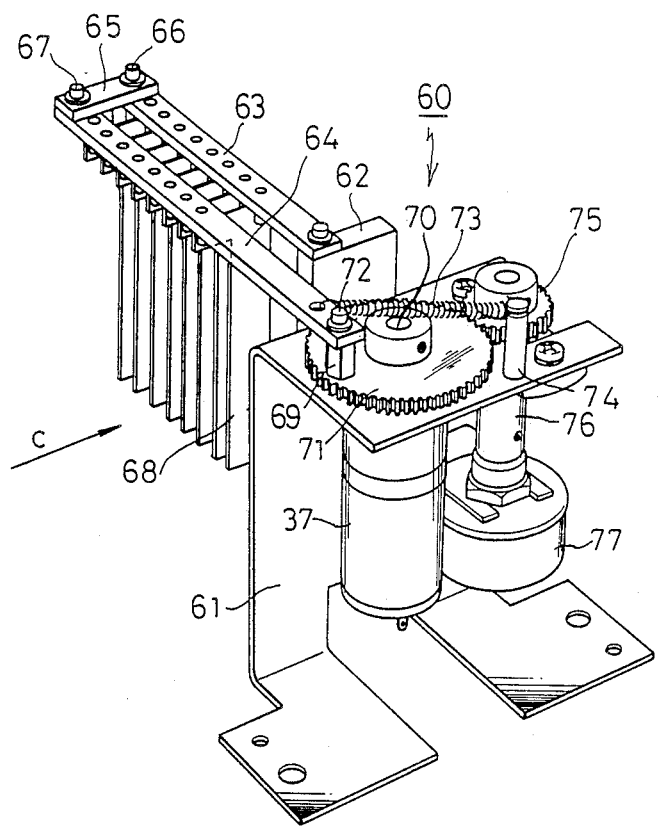
FIG. 12 is a perspective view, seen from the opposite direction to that of FIG. 11.

In FIGS. 11 and 12, there is shown one embodiment of the illuminance control device 60. A pair of fixed mount members 63 are secured in parallel to a frame 61 through a bracket 62 in a vertical plane so as to extend from the bracket 62 in the horizontal direction, and a movable mount member 64 is pivotally mounted to the upper fixed mount member 63 in parallel therewith via a link member 65 which pivotally connects one ends of the two mount members 63 and 64 through pivot pins 66 and 67. A plurality of shutter plates 68 are pivotally mounted in parallel to one another to the fixed and movable mount members 63 and 64 at a certain interval in the vertical direction. The other end of the movable member 64 is pivotally connected to a stud 69 secured to a peripheral portion of a gear wheel 71 via a pivot pin 72 secured to the stud 69. The gear wheel 71 is secured to a rotary shaft 70 of the drive motor 37 mounted to the frame 61.

Figure 13:
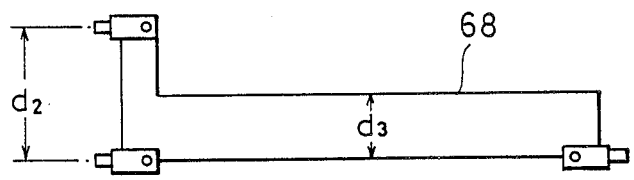
FIG. 13 is an elevational view of a shutter plate shown in FIG. 11.

The other end portion of the movable mount member 64 is biased towards the rotary shaft 70 of the drive motor 37 by a spring member 73 extended between the other end portion of the movable mount member 64 and a pin 74 fixed to the frame 61 in order to improve the accuracy of the slide movement of the movable mount member 64. The gear wheel 71 is engaged with another gear wheel 75 mounted to a rotary shaft 76 of the potentiometer 77 mounted to the frame 61. The shutter plate 68 is shown in FIG. 13.

The potentiometer 77 detects the open-close position of the shutter plates 68 and outputs a signal corresponding to the open-close position of the shutter plates 68 to the driver 25 and the integrator 24. The illumination of the light beam to be fed to the light guide is controlled by the shutter plates 68 and may be always displayed on the display 23 and the open-close position of the shutter plates 68 is controlled on the basis of the detection of the open-close position of the shutter plates 68 by the potentiometer 68.

In this embodiment, the fixed mount members 63, the movable mount member 64 and the shutter plates 68 mounted thereto constitute a diaphragm, and the fixed mount members 63, the movable mount member 64, the link member 65, the pivot pins 66, 67 and 72, the stud 69 and the gear wheel 71 constitute a diaphragm controller.

In FIGS. 10 to 12, the light beam 34 emitted by the lamp 32 is passed to the light guide 14 through the slits formed by the shutter plates 68 arranged in the light path of the light beam in a direction indicated by an arrow c in FIGS. 10 and 11, perpendicular to the fixed mount members 63. When the shutter plates 68 are positioned perpendicular to the fixed mount members 63, the shutter plates 68 are positioned in the maximum opening position and the illuminance of the light beam 34 passing through the slits between the shutter plates 68 becomes the maximum value as long as the light intensity of the light beam generated by the lamp 32 is constant.

Now, when the integrator 24 detects that the illuminance of the light beam illuminated to the object is too much on the basis of the output signal of the potentiometer 76, and thus sends a drive signal for reducing the illuminance of the light beam to the driver 25, the driver 25 drives the drive motor 37 to rotate the gear wheel 71. Then, the movable mount member 64, which is pivotally connected to the gear wheel 71 through the stud 69 and the link pin 72, is slidably moved in cooperation with the link member 65 and the spring member 73 to equally narrow or reduce the slits between the shutter plates 68, i.e., to uniformly cut the light path of the light beam 34, and thereby the illuminance of the light beam 34 to be fed to the light guide is reduced to the desired intensity.

Then, when the illuminance of the light beam is to be increased, an instruction for reversely rotating the drive motor 37 is given to the drive motor 37, and the drive motor 37 is rotated in the reverse direction to rotate the gear wheel 71 in the reverse direction. Thus, the movable member 64 is slid in the opposite direction to widen or open the slits between the shutter plates 68, and the illuminance of the light beam 34 to be fed to the light guide 14 is increased.

Figure 14:
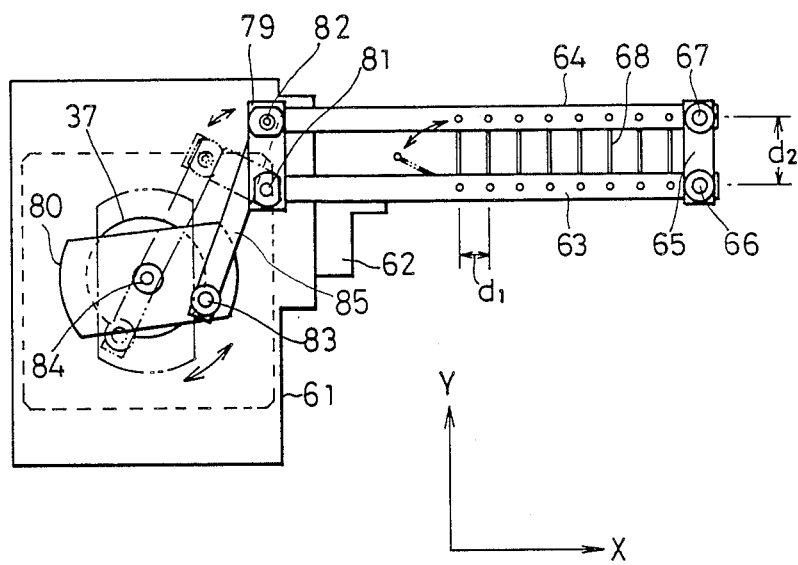
FIG. 14 is a schematic top plan view of another embodiment of the illuminance control device used in the illuminance controller for the light source shown in FIG. 10.

FIG. 14 is a top plan view of another embodiment of the illuminance control device 60 having a similar structure to the embodiment shown in FIGS. 11 and 12. In this case, the upper fixed mount member 63 has the same length as the movable mount member 64, and another link member 79 connects the other ends of these two mount members 63 and 64 via pivot pins 81 and 82. As a result, the upper mount member 63, the movable mount member 64, the two link members 65 and 79 and the pivot pins 66, 67, 81 and 82 form a parallelogrammic frame. The shutter plates 68 are arranged in parallel with the link members 65 and 79. A plate member 80 is secured to the drive motor 37 through a rotary shaft 84, and a pivot pin 83 is mounted to an offset position from the rotary shaft 84 of the drive motor 37. An arm member 85 pivotally links the pivot pins 82 and 83.

In this embodiment, by rotating the drive motor 37 in a clockwise or counterclockwise direction, the movable mount member 64 is slidably moved through the rotary shaft 84, the plate member 80, the arm member 85 and the pivot pins 82 and 83, and the width of the slits between the shutter plates 68 are controlled. Hence, the illuminance of the light beam 34 to be fed to the light guide 14 is controlled to the desired value in the same manner as the embodiment shown in FIGS. 11 and 12.

In this embodiment, the interval $d_1$ of the shutter plates 68, the distance $d_2$ of the two pivot pins 81 and 82 or the two mount members 63 and 64, and the width $d_3$ of the shutter plate 68 are suitably determined, and the positions of the pivot pins 81, 82 and 83 and the rotary shaft 84 of the drive motor 37 are also suitably determined.

In FIG. 14, now, the necessary actual dimensions of Examples 1 to 3 of the illuminance control device 60 will be described. That is, assuming that the axes of X and Y coordinates are defined in the direction of the extension of the fixed mount member 63 and the direction perpendicular thereto, respectively, and that the coordinates of the position of the pivot pin 81 as the point 81 are defined to (0,0), when the shutter plates 68 were opened to the maximum or were positioned perpendicular to the fixed mount members 63, the distances $d_1$, $d_2$ and $d_3$ were defined to common values 5.0 mm, 11.0 mm and 5.5 mm, respectively, and the coordinates of the points of the pivot pins 82 and 83 and the rotary shaft 84, hereinafter referred to as the points 82, 83 and 84, in Examples 1 to 3 were determined in the following Table:

TABLE 1

|  | Example 1 | Example 2 | Example 3 |
|---|---|---|---|
| Point 81 | (0, 0) | (0, 0) | (0, 0) |
| Point 82 | (0, 11.0) | (0, 11.0) | (0, 11.0) |
| Point 83 | (−11.0, −19.4) | (−8.2, −16.5) | (−8.2, −11.8) |
| Point 84 | (−20.0, −15.0) | (−16.0, −15.0) | (−16.0, −10.0) |
| Curve | D | E | F |

Figure 15:
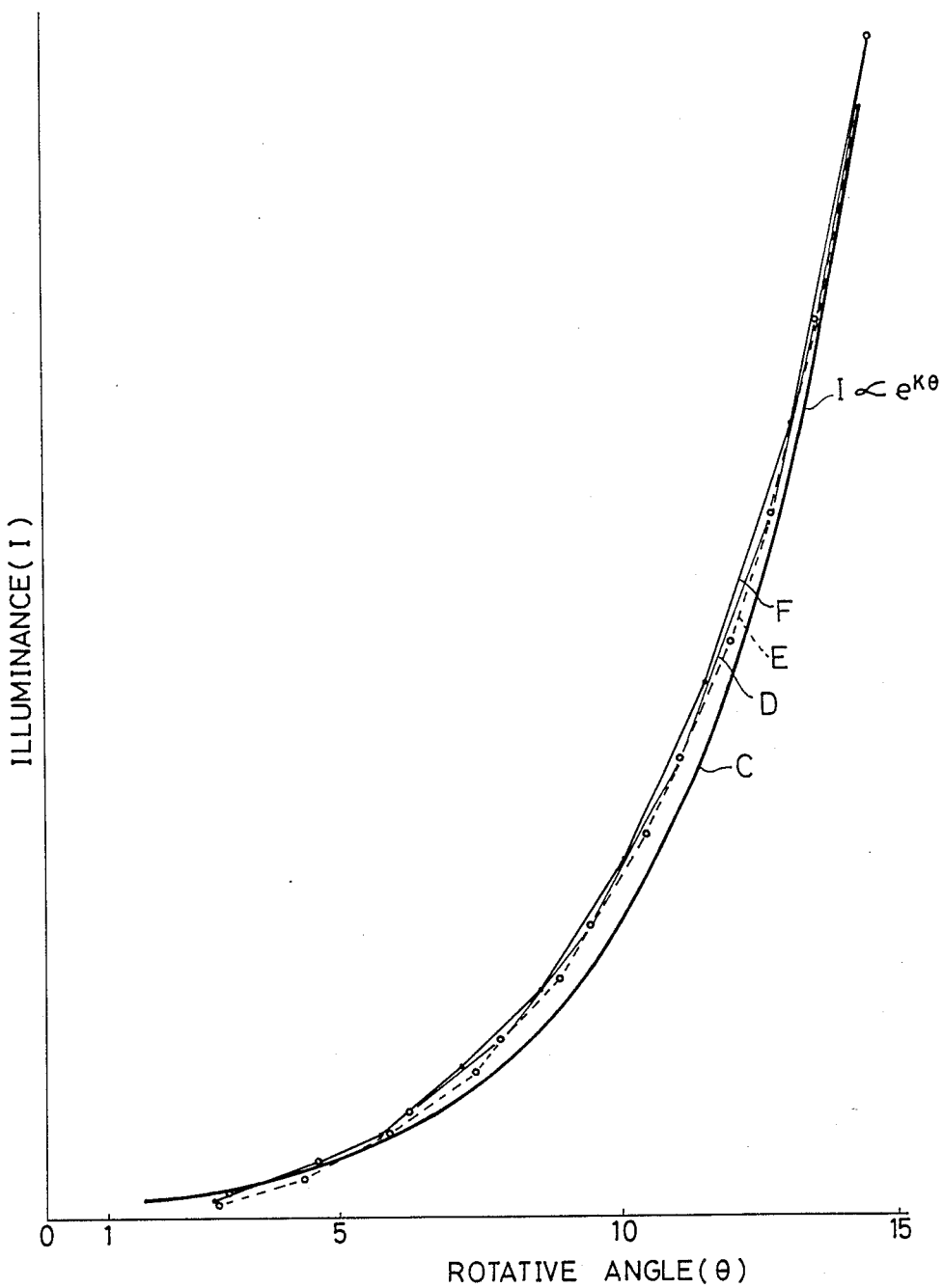
FIG. 15 is a graphical representation showing the relation between the rotative angle and the illuminance of the diaphragm of the illuminance control device of FIG. 14.

In Examples 1 to 3, the distances between the two points 83 and 84 became approximately 8 mm, 8 mm and 10 mm, respectively, and the distances between the two points 82 and 83 became approximately 32.6 mm, 28.8 mm and 24.2 mm, respectively. In FIG. 15, the relations between the illuminance I of the light beam 34 to be fed to the light guide 14 and the rotative angle $\theta$ of the drive motor 37 of Examples 1 to 3 are represented by respective curves D, E and F, as tabulated in Table 1, in which a curve C represents the ideal relation, i.e., $I\alpha e^{K\theta}$ in the same manner as the curve B in FIG. 6. The curves D, E and F are almost the same as the ideal curve C, as shown in FIG. 15, and thus the problems such as the overshoot, the hunting and the responsive time lag can be effectively prevented.

As described above in connection with the second embodiment of the illuminance controller according to the present invention, the illuminance of the light beam can be accurately and readily controlled by changing the open-close angle of the shutter plates with respect to the direction of the optical axis, and the illuminance of the light beam can be uniformly controlled by uniformly cutting the light path of the light beam sliced by the shutter plates to obtain the uniform illuminance distribution of the light beam to be lighted to the object without causing any problem such as overshoot, a hunting or a responsive time lag. Therefore, the observing accuracy of the object can be extremely improved during the operation of the endoscope.

Figure 16:
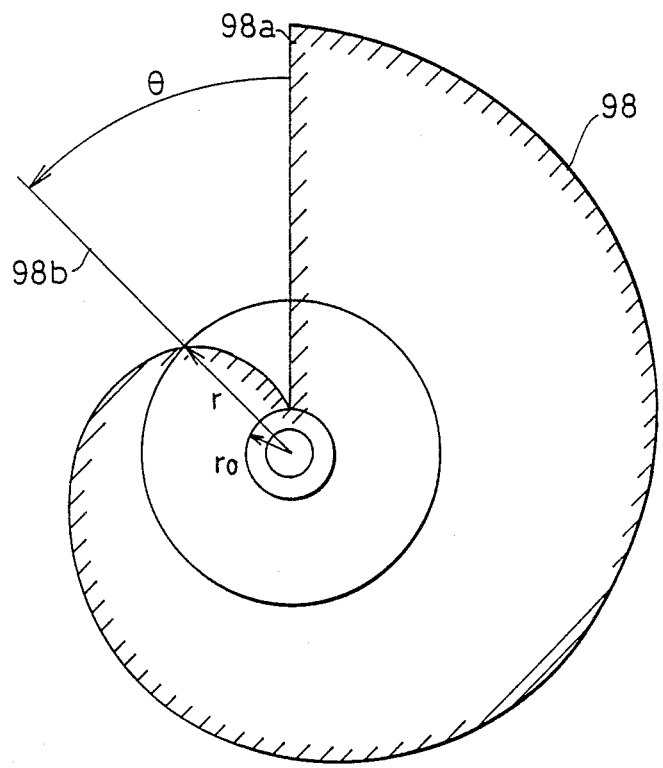
FIG. 16 is an elevational view of one embodiment of a rotary shutter plate used as a diaphragm of still another embodiment of an illuminance controller for a light source according to the present invention.
Figure 17:
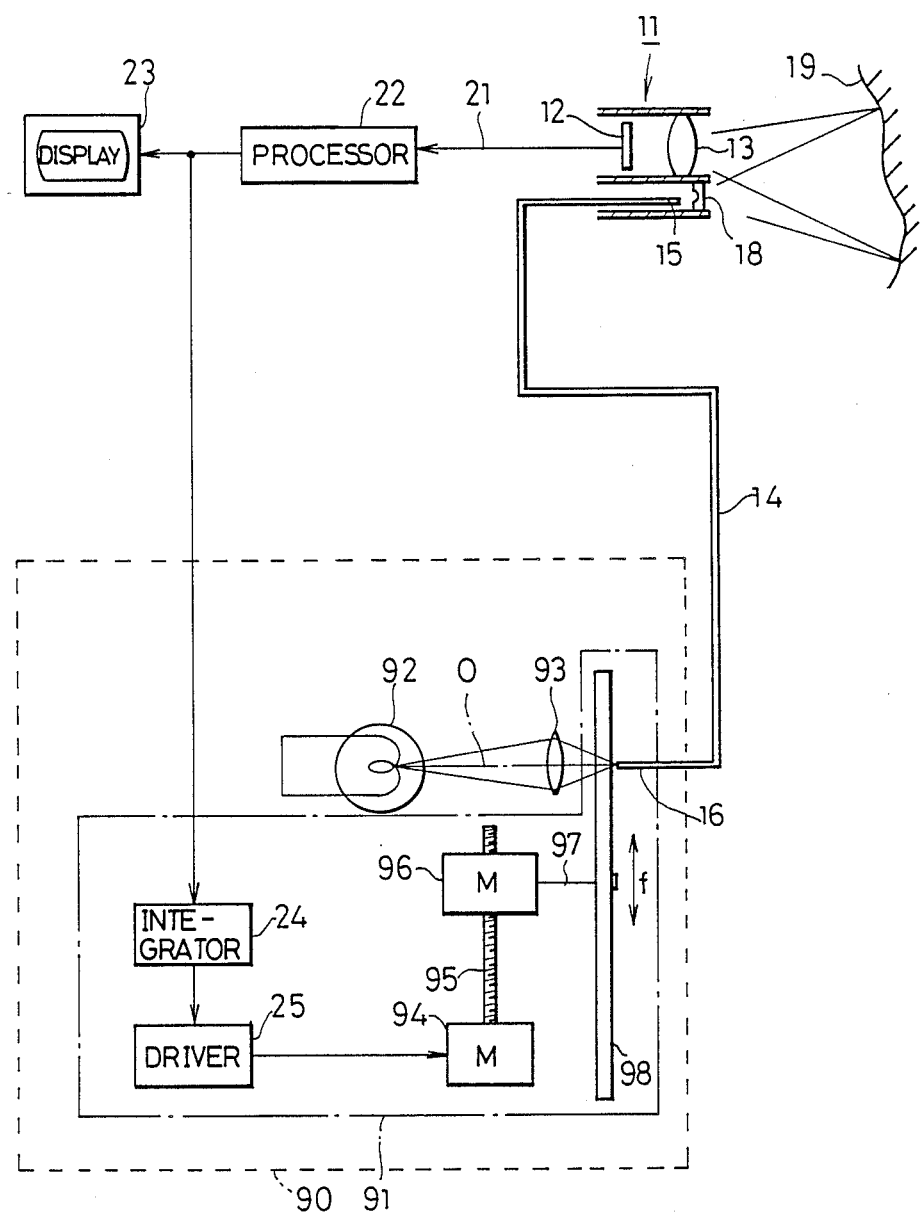
FIG. 17 is a schematic block diagram of another endoscope including still another embodiment of an illuminance controller for a light source according to the present invention.

In FIG. 17, there is shown another endoscope including the third embodiment of the illuminance controller for the light source according to the present invention. FIG. 16 shows one embodiment of a rotary shutter plate having a spiral periphery for use as a diaphragm in the illuminance controller shown in FIG. 17.

As shown in FIG. 16, in the rotary shutter plate 98, an opening angle $\theta$ is defined by an initial side 98a of the angle $\theta$ and an angle generating line 98b passing through the center of the rotary shutter plate 98 and an intersection of the spiral periphery of the rotary shutter plate 98 and the circumference of a circle having a radius r around the center of the rotary shutter plate 98. The opening angle $\theta$ corresponding to the irradiation time or the illuminance I of the light beam to be fed to the light guide is formed to a proper shape so as to satisfy a formula $\theta \alpha \exp^{k(r-r_0)}$, wherein k is constant, $r_0$ is the minimum value of the radius r, and $r-r_0$ is an effective axial distance, as shown by a curve H in FIG. 18.

In FIG. 17, the endoscope has a similar construction to the one shown in FIG. 7. A light source 90 includes a light source portion 92 comprised of a xenon lamp or the like for generating a light beam, and a condenser lens 93 for focusing the light beam to the rear end 16 of the light guide 14. An illuminance control device 91 includes the rotary shutter plate 98 arranged between the condenser lens 93 and the rear end 16 of the light guide 14, for cutting the light path along the optical axis O of the light beam, and a drive motor 96 for rotating the rotary shutter plate 98 at a constant speed. The rotary shutter plate 98 is secured to a rotary shaft 97 of the drive motor 96. The illuminance control device 91 also includes a controller for changing an axial distance between the optical axis of the light beam and the rotary axis of the rotary shutter plate 98, as indicated by an arrow f in FIG. 17, the controller comprising a slide member 95 such as a screw rod for slidably supporting the drive motor 96, and a reversible motor 94 for rotating the slide member 95 in both directions. The illuminance control device 91 further includes, as a feedback device, an integrator 24 for operating the illuminance of the picture and a driver 25 for driving the reversible motor 94.

In this embodiment, the light beam incident to the rear end 16 of the light guide 14 is emitted from its front end 15 to an object 19 through a lighting window 18, and the light reflected from the object 19 is picked up by a CCD 12 through an object lens 13 in the same manner as described above.

Figure 5:
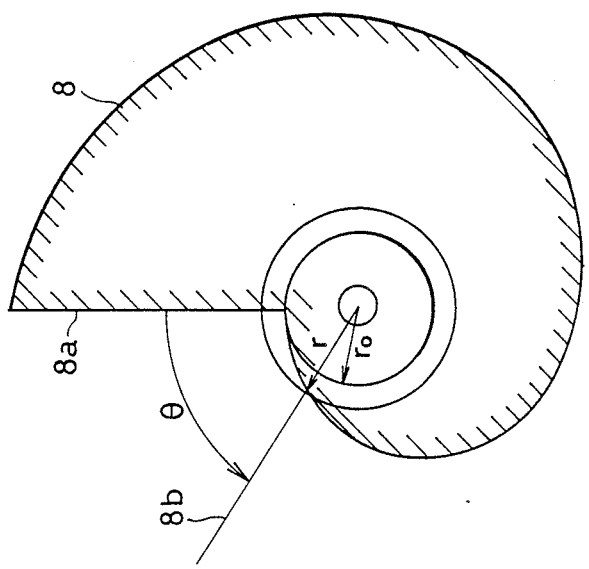
FIG. 5 is an elevational view of a conventional rotary shutter plate used in an illuminance controller of the light source for use in the endoscope.
Figure 18:
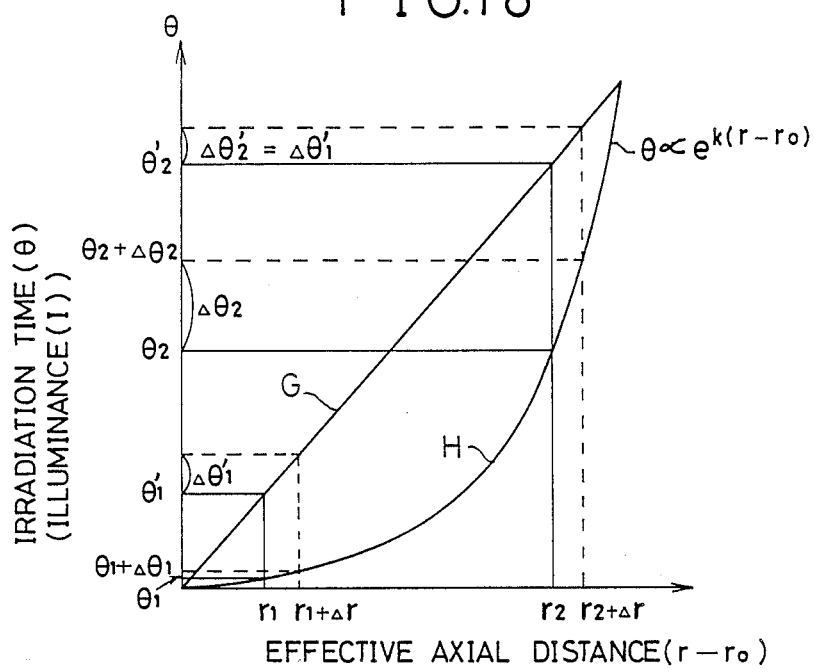
FIG. 18 is a graphical representation showing a relation between an effective axial distance and an irradiation time of the rotary shutter plate of FIG. 16 in comparison with the conventional rotary shutter plate of FIG. 5.

In FIG. 18, there is shown the relation between the effective axial distance $r-r_0$ and the irradiation time $\theta$ of the rotary shutter plate 98 shown in FIG. 16 for use in the present invention in comparison with the conventional rotary shutter plate 8 shown in FIG. 5 when the rotary shutter is rotated at a constant speed. Since the illuminance of the light beam is in proportion to its irradiation time when the luminous intensity of the light beam generated by the light source is constant, the irradiation time of the light beam is represented by the opening angle $\theta$ of the rotary shutter plate 98.

The line G represents the characteristics of the conventional rotary shutter plate 8, satisfying the formula $\theta = k(r-r_0)$. In this case, as shown in FIG. 18, when the effective axial distances are $r_1$ and $r_2$, the respective irradiation times become $\theta_1'$ and $\theta_2'$, and the variation of the irradiation time corresponding to the minute variation $\Delta r$ of the effective axial distance is an equal value $\Delta \theta_1'$. Thus, the relative values of the variation rates of the two effective axial distances are written as follows:

$$\Delta \theta_1'/\theta_1' : \Delta \theta_1'/\theta_2' = \theta_2':\theta_1' = r_2:r_1$$

Accordingly, the variations may be varied in various ways depending on the effective axial distance.

On the other hand, according to the present invention, the characteristics of the rotary shutter plate 98 is represented by the curve H satisfying the formula $\theta \alpha \exp^{k(r-r_0)}$. When the effective axial distances are $r_1$ and $r_2$, the relative values of of the variation rates of the two effective axial distances are written as follows:

$$\Delta \theta_1/\theta_1 = \Delta \theta_2/\theta_2 = k(\text{constant})$$

Hence, the variation rate of the illuminance of the light beam becomes constant regardless of the effective axial distance.

In FIG. 17, the picture signals picked up by the CCD 12 are sent to the signal processor 22, and the processor 22 outputs the processed signals to the display 23 and the integrator 24. In the integrator 24, all illuminance of picture elements contained in the picture is integrated, and then the brightness of the picture is discriminated. Then, the integrator 24 sends a signal for controlling the illuminance of the light beam to the driver 25 as a feedback, and the driver 25 outputs a regular or reverse drive signal to the reversible motor 94 to move the drive motor 96 along with the rotary shutter plate 98 in the direction indicated by the arrow f, thereby changing the axial distance between the optical axis O of the light beam and the rotary axis of the rotary shutter plate 98 to the proper value. In this case, when the rotary shutter plate 98 is rotated at the constant speed, it cuts the light path of the light beam to produce the pulsed light beam.

Therefore, the cutting or shading time of the light path of the light beam can be freely controlled, and thus the irradiation time, i.e., the illumination of the pulsed light beam can be controlled at will depending on the brightness of the picture of the object.

As described above, the illuminance of the light beam to be fed to the light guide can be readily and accurately controlled depending on the object to be observed without causing the problems such as the overshoot, the hunting and the responsive lag.

Figure 19:
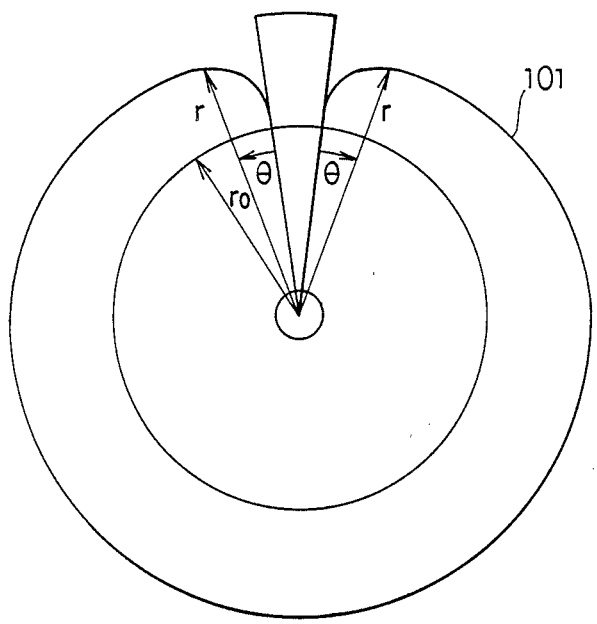
FIGS. 19 to 21 show other embodiments of a rotary shutter plate used in the illuminance controller of FIG. 17.
Figure 20:
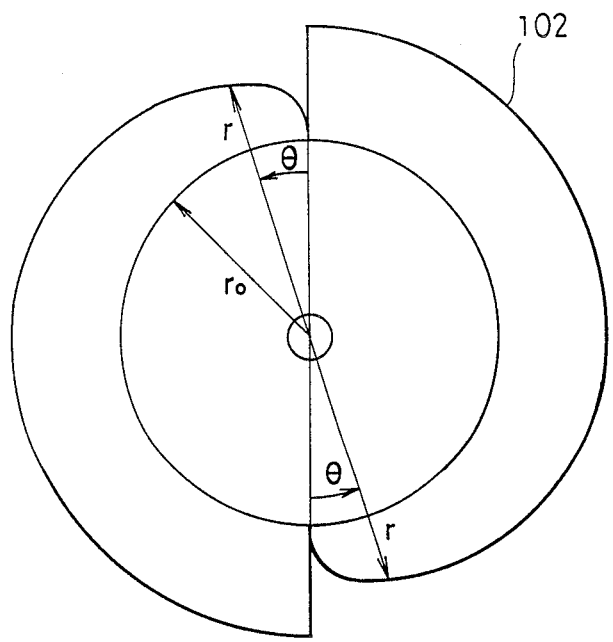
Figure 21:
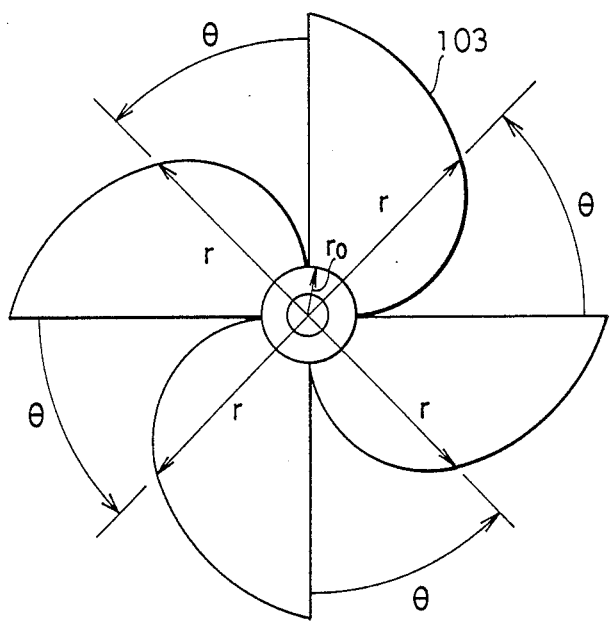

In FIGS. 19 to 21, there are shown other embodiments of the rotary shutter plate used in the illuminance control device shown in FIG. 17.

As shown in FIG. 19, a rotary shutter plate 101 produces two pulses of the light beam per one rotation. In this case, the two pulses of the light beam are successively produced at a short interval so as to prevent an appearance of a blurring of a picture, and thus the rotary shutter plate 101 is preferably used in a two-field photographing system, in which a frame of picture is composed of two fields of odd and even numbers.

In FIG. 20, another rotary shutter plate 102 produces two pulses of the light beam every one rotation at an equal interval.

As shown in FIG. 21, a further rotary shutter plate 103 can produce four pulses of the light beam per one rotation at an equal interval.

In these embodiments shown in FIGS. 19 to 21, the substantially constant variation rate of the illumination time can be always obtained irrespective of the effective axial distance in the same manner as the embodiment shown in FIG. 16, and the same effects and advantages as those of the embodiment of FIG. 16 can be, of course, obtained.

From the above description of the preferred embodiments of the present invention, it is readily understood that an illuminance of a light beam can be accurately and readily controlled without causing any problem such as an overshoot, a hunting and a responsive lag, and a uniform illuminance distribution of a light beam can be produced over an entire illuminated area, and that a quick response can be readily obtained in an automatic illuminance control system.

Although the present invention has been described in its preferred embodiments with reference to the accompanying drawings, it is readily understood that the present invention is not restricted to the preferred embodiments above-described and that various changes and modifications may be made in the present invention by a person skilled in the art without departing from the spirit and scope of the present invention.

What is claimed is:

1. An illuminance controller for a light source, comprising:
a diaphragm for cutting a light beam generated by a light source to control an illuminance of the light beam;
diaphragm control means for controlling a light beam cut amount of the diaphragm; and
drive means for driving the diaphragm, the illuminance of the light beam cut by the diaphragm varying with respect to a driving amount of the drive means in accordance with an exponential function.

2. An illuminance controller for a light source, comprising:
a diaphragm for cutting a light beam generated by a light source to control an illuminance of the light beam;
diaphragm control means for controlling a light beam cut amount of the diaphragm; and
drive means for driving the diaphragm control means, the illuminance I of the light beam cut by the diaphragm varying with respect to a rotative angle $\theta$ of the drive means in accordance with a formula $I \alpha \exp^{K\theta}$, wherein K is constant.

3. The controller of claim 2, wherein the diaphragm control means includes a cam member having a spiral guide groove thereon, connected to a rotary shaft of the drive means, a pivot arm pivotally mounted to a pivot pin, and a guide pin connected to one end of the pivot arm, for engaging with the spiral guide groove, the other end of the pivot arm being connected to the diaphragm.

4. The controller of claim 2, wherein the diaphragm control means includes a cam member having a spiral periphery, connected to a rotary shaft of the drive means, a pivot arm pivotally mounted to a pivot pin, and a slider which is connected to one end of the pivot arm and is biased onto the spiral periphery of the cam member through a spring, the other end of the pivot arm being connected to the diaphragm via a pivot point.

5. The controller of claim 2, wherein the diaphragm comprises a fishtail-like shutter plate.

6. The controller of claim 2, wherein the diaphragm includes at least two shutter plates pivotally arranged in parallel to one another to open or close slits defined by the shutter plates for cutting the light beam.

7. The controller of claim 6, wherein the diaphragm control means includes a fixed mount member, a movable mount member pivotally connected thereto through a link member, and an arm member pivotally connect the movable mount member with the drive means, the movable mount member being slidably moved by the drive means through the arm member to open or close the slits between the shutter plates for cutting the light beam.

8. The controller of claim 7, wherein the diaphragm control means also includes a potentiometer for detecting an open-close amount of the slits between the shutter plates from a driving amount of the drive means.

9. An illuminance controller for a light source, comprising:
a diaphragm for cutting a light beam generated by a light source to control an illuminance of the light beam;
drive means for driving the diaphragm; and
diaphragm control means for controlling a light beam cut amount of the diaphragm, the illuminance I of the light beam cut by the diaphragm varying with respect to an axial distance R between an optical axis of the light beam and a rotary axis of the diaphragm in accordance with a formula $I\alpha exp^{kR}$, wherein k is constant.

10. The controller of claim 9, wherein the diaphragm comprises a rotary shutter plate mounted to a rotary shaft of the drive means, the rotary shutter plate including a center, a spiral periphery, an opening angle $\theta$ and and an initial side of the opening angle $\theta$, the opening angle being defined by the initial side and an angle generating line passing through the center and a points on the spiral periphery, and wherein the illuminance I of the light beam is proportion to the opening angle $\theta$ of the rotary shutter plate.

11. The controller of claim 10, wherein the axial distance R is $r - r_0$, wherein r is a distance between the center and an intersection of the angle generating line and the spiral periphery, and $r_0$ is a distance between the center and an intersection of the angle generating line and the spiral periphery when the opening angle is 0 degree.

12. The controller of claim 11, the diaphragm control means includes a slide member for slidably supporting the drive means, and a reversible motor for moving the drive means via the slide member in a direction of the extension of the rotary shutter plate to control the axial distance R.

13. An endoscope, comprising:
a scope for observing an object in an inside of an internal organ and picking up picture signals thereof;
a light source for generating a light beam to the scope;
a processing unit for operating the picture signals picked up by the scope; and
an illuminance controller for the light source, including:
a diaphragm for cutting the light beam generated by the light source to control an illuminance of the light beam;
diaphragm control means for controlling a light beam cut amount of the diaphragm; and
drive means for driving the diaphragm, the illuminance of the light beam cut by the diaphragm varying with respect to a drive amount of the drive means in accordance with an exponential function.

* * * * *